(12) United States Patent
Thiebes et al.

(10) Patent No.: US 6,833,455 B2
(45) Date of Patent: Dec. 21, 2004

(54) BRIDGED PERINONES/QUINOPHTHALONES

(75) Inventors: Christoph Thiebes, Köln (DE); Josef-Walter Stawitz, Odenthal (DE); Ulrich Feldhues, Gladbach (DE)

(73) Assignee: Bayer Aktiengesellschaft, Leverkusen (DE)

( * ) Notice: Subject to any disclaimer, the term of this patent is extended or adjusted under 35 U.S.C. 154(b) by 8 days.

(21) Appl. No.: 10/302,186

(22) Filed: Nov. 22, 2002

(65) Prior Publication Data

US 2003/0139498 A1 Jul. 24, 2003

(30) Foreign Application Priority Data

Nov. 27, 2001  (DE) .......................................... 101 58 137

(51) Int. Cl.[7] ..................... C07D 401/12; C07D 403/12
(52) U.S. Cl. ...................... 546/101; 546/110; 546/154; 546/173; 546/174; 544/245; 548/301.7; 8/689; 106/31.27; 106/287.21
(58) Field of Search .................... 106/31.27, 287.21; 544/245; 546/157, 173, 101, 110, 154, 174; 548/301.7; 8/689

(56) References Cited

U.S. PATENT DOCUMENTS

| 5,621,027 A | * | 4/1997 | Roschger et al. | ............. 524/90 |
| 5,948,597 A | * | 9/1999 | Itoh et al. | ................. 430/281.1 |
| 5,955,614 A | * | 9/1999 | Kalz et al. | ................... 546/173 |

OTHER PUBLICATIONS

Manukian B K et al: "Chinophthalone" Chimia, AARAU, Ch. Bd.24, Nr. 9, 1970, Seiten 328–339, XP002073520 ISSN: 0009–4293 Verbindungen XXXV and XXXVI, Seite 337.

Shigenori Otsuka et al: "A New Double Layer Photoconductor System with Advanced Reliability Using Perinone Bisazopigment in the Carrier Generation Layer" Proceedings of the International Congress on Advances in Non Impact Printing Technologies. San Francisco, Aug. 24–28, 1986, Springfield, SPSE, US. Bd. Congress 3, Aug. 24, 1986, Seiten 16–24, XP000222791 Verbindung III< Seite 17.

* cited by examiner

Primary Examiner—Thomas McKenzie
(74) Attorney, Agent, or Firm—Godfried R. Akorli; Diderico van Eyl

(57) ABSTRACT

Disclosed herein are bridged perinones/quinophthalones of the general formula (I) or tautomeric forms thereof

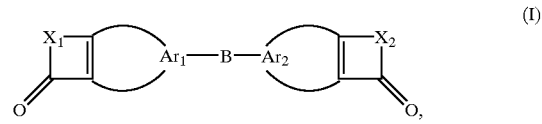

(I)

where X1, X2, $Ar_1$ $Ar_2$ and B are as described herein and are particularly characterized in that the bridging B is a radical of the formula $-T_1-W-T_2-$, where $T_1$ and $T_2$ are independently O or S and W is alkylene, especially $C_1-C_6$-alkylene, $C_6-C_{10}$-arylene, especially phenylene or cycloalkylene, which are each optionally substituted or is the radical of the formula (a)

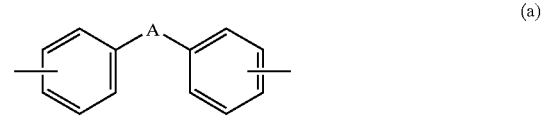

(a)

where the phenyl rings are optionally substituted and

A is a radical of the formula O, S, SO, $SO_2$ or CO, optionally substituted alkylene, or optionally substituted cycloalkylene, said alkylene or cycloalkylene being attached to the adjacent phenyl rings itself or else via its substitutents, or W is a radical of the formulae

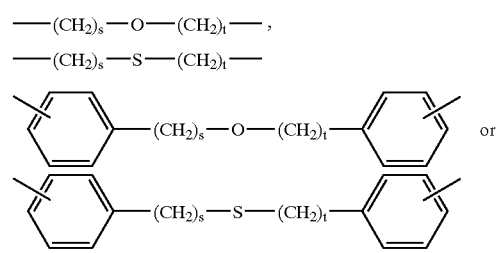

where s and t are independently from 1 to 6, the ends of the radical B each being attached to an aromatic carbon atom of the two radicals $Ar_1$ and $Ar_2$. EINBETTENEINBETTEN

34 Claims, No Drawings

BRIDGED PERINONES/ QUINOPHTHALONES

BACKGROUND OF THE INVENTION

1. Field of the Invention

The invention relates to bridged perinones, quinophthalones and perinone-quinophthalones, processes for their preparation and their use for mass coloration of plastics.

2. Brief Description of the Prior Art

It is known to use perinone dyes as described for example in FR-A-1 075 110 or U.S. Pat. No. 5,466,805 for mass coloration of plastics. It is also known to use quinophthalone dyes as described for example in DE-A-44 35 714 or DE-A-21 32 681 for mass coloration of plastics. Compounds of this type are notable for good thermal stability and high light fastness, but their sublimation fastness is still in need of improvement. Illustratively, temperatures of above 240° C. which occur in the coloration process in the injection moulding machines, lead all too commonly to an undesirable sublimation of the dye, contaminating the working equipment and necessitating costly and inconvenient cleaning measures. EP-A-827 986 already discloses doubled quinophthalone and perinone dyes possessing good sublimation fastness.

It is an object of the present invention to provide further sublimation-fast dyes for the mass coloration of plastic, which are preferably readily soluble in the monomeric starting materials of the plastic too in order that greater flexibility in the coloration of plastics may be ensured.

SUMMARY OF THE INVENTION

There have now been found compounds of the general formula (I) or tautomeric forms thereof

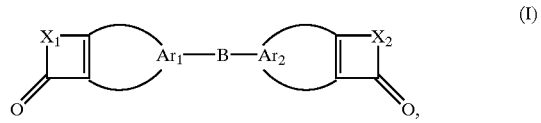

(I)

where $Ar_1$ and $Ar_2$ are independently radicals needed to complete optionally substituted carbocyclic aromatics, B is a radical of the formula $-T_1-W-T_2-$, where $T_1$ and $T_2$ are independently O or S and W is alkylene, especially $C_1-C_6$-alkylene, $C_6-C_{10}$-arylene, especially phenylene or cycloalkylene, which are each optionally substituted or is the radical of the formula (a)

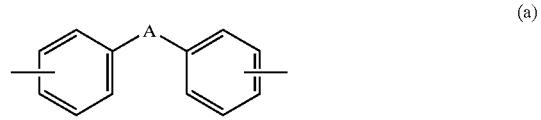

(a)

where the phenyl rings are optionally substituted and A is a radical of the formula O, S, SO, $SO_2$ or CO, optionally substituted alkylene, or optionally substituted cycloalkylene, said alkylene or cycloalkylene being attached to the adjacent phenyl rings itself or else via its substituents, or W is a radical of the formulae

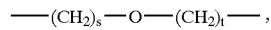
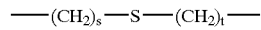

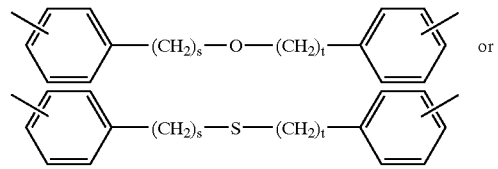 or

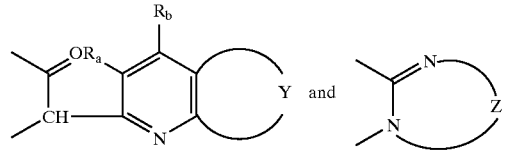

where
s and t are independently from 1 to 6,
the ends of the radical B each being attached to an aromatic carbon atom of the two radicals $Ar_1$ and $Ar_2$, and $X_1$ and $X_2$ are independently a radical of the formulae selected from the group consisting of

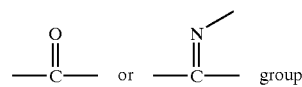   Y and each being located in the ring in such a way that the $$-\overset{O}{\underset{\|}{C}}-\quad \text{or} \quad -\overset{N}{\underset{\|}{C}}-\quad \text{group}$$

is adjacent to the C—C double bond,
where

Y is a radical of an optionally substituted benzene or naphthalene ring,
Z is optionally substituted ortho-phenylene, ortho-naphthylene, peri-(1,8)-naphthylene or arylene composed of more than two fused-together benzene rings, aryl radicals which have more than two fused-together benzene rings being bridged ortho or in a manner corresponding to a peri position in naphthalene,
$R_a$ is H or OH, and
$R_b$ is H or halogen, especially F, Br or Cl.

The peri position actually denotes the 1,8-position in naphthalene. Both in the literature and in the context of the present application, however, this meaning is extended to include arylenes composed of more than two fused-together benzene rings.

Possible substituents for Z and for the two phenyl rings of the radical of the formula (a) include for example: $C_1-C_6$-alkyl, halogen, nitro, aryl, aryloxysulphonyl, hydroxyl, $C_1-C_6$-alkoxy, aryloxy, optionally alkyl- or acyl-substituted amino, optionally alkyl- or aryl-substituted aminosulphonyl, optionally alkyl-substituted carboxamide or a fused-on aromatic, cycloaliphatic or heterocyclic ring.

Preferred substituents are: chlorine, bromine, nitro, methoxy, $NH_2$, benzyloxy, hydroxyl, $-SO_2O(C_6H_5)$, $-SO_2N(CH_3)_2$, $-SO_2NHCH_3$, methyl, ethyl, n-propyl, iso-propyl, n-butyl, sec-butyl, tert-butyl, $NHCOCH_3$, $-N(C_2H_5)_2$ or optionally substituted phenyl.

Possible substituents for the benzene or naphthalene radical completed by Y include for example: halogen, especially Cl and Br, —COOH, —COOR, where R is $C_1$–$C_{10}$alkyl, preferably $C_1$–$C_4$-alkyl, especially methyl or ethyl, $C_6$–$C_{10}$-aryl or $C_5$-$C_8$-cycloalkyl, and $C_1$–$C_6$-alkyl, especially methyl.

Possible substituents for the carbocyclic aromatic completed by $Ar_1$ and Ar2 include for example: $C_1$–$C_6$-alkyl, especially methyl, ethyl, n-propyl, iso-propyl, n-butyl, sec-butyl and tert-butyl, halogen, especially Cl or Br, alkylcarbonyl, arylcarbonyl, alkylsulphonyl, arylsulphonyl, nitro, aryl, especially optionally substituted phenyl, aryloxysulphonyl, especially —$SO_2OC_6H_5$, hydroxyl, $C_1$–$C_6$-alkoxy, such as methoxy or benzyloxy, aryloxy, such as phenoxy, optionally alkyl- or acyl-substituted amino such as $NH_2$, $NHCOCH_3$ or —$N(C_2H_5)_2$, optionally alkyl- or aryl-substituted aminosulphonyl such as $SO_2N(CH_3)_2$ or $SO_2NHCH_3$ or a fused-on aromatic, cycloaliphatic or heterocyclic ring.

Particularly preferably $Ar_1$ and Ar2 are independently a radical needed to complete an optionally substituted benzene or naphthalene ring, especially an optionally substituted benzene ring.

Possible substituents for the alkylene group in W and A, which can be not only straight-chain but also branched, include for example halogen such as F or Cl, $CF_3$, O, S, optionally substituted phenyl and $C_1$–$C_6$-alkyl.

Possible substituents for the cycloalkyl group, especially the $C_5$–$C_6$-cycloalkylene group, particularly preferably the cyclohexylidene group, include for example one or more $C_1$–$C_4$-alkyl radicals.

Particular preference is given to compounds of the formula (I) which conform to the formula (II) or tautomeric forms thereof

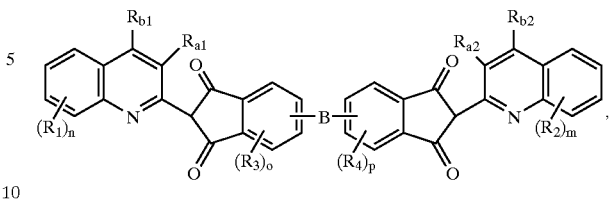

(II)

where $Y_1$ and $Y_2$ are independently the radical of an optionally substituted benzene or naphthalene ring,
$R_{a1}$ and $R_{a2}$ are independently H or OH, and
$R_{b1}$ and $R_{b2}$ are independently H or halogen, especially Br or Cl and
$Ar_1$, $Ar_2$ and B are each as defined above.

Possible substituents for the radicals $Y_1$ and $Y_2$ are for example the substituents indicated for the radical Y.

Particularly preferably $R_{b1}$ and $R_{b2}$ are each hydrogen.

Particular preference is given to compounds of the formula (II) which conform to the formula (IIa) or tautomeric forms thereof

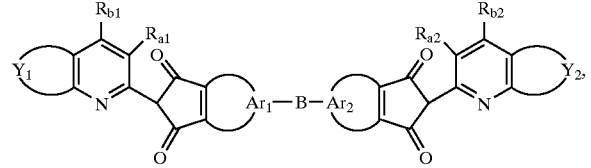

(IIa)

where n and m are independently from 0 to 4,
$R_1$ and $R_2$ each independently have the same or different meanings as indicated for the substituents for the radicals completed by $Y_1$ and $Y_2$,
o and p are independently from 0 to 2, especially 0 or 1,
$R_3$ and $R_4$ each independently have the same or different meanings as indicated for the substituents for the carbocyclic aromatics completed by $Ar_1$ and $Ar_2$,
$R_{b1}$ and $R_{b2}$ are each as defined above and are preferably H,
$R_{a1}$ and $R_{a2}$ are each as defined above and are preferably OH, and
B is as defined above. The preferred B include

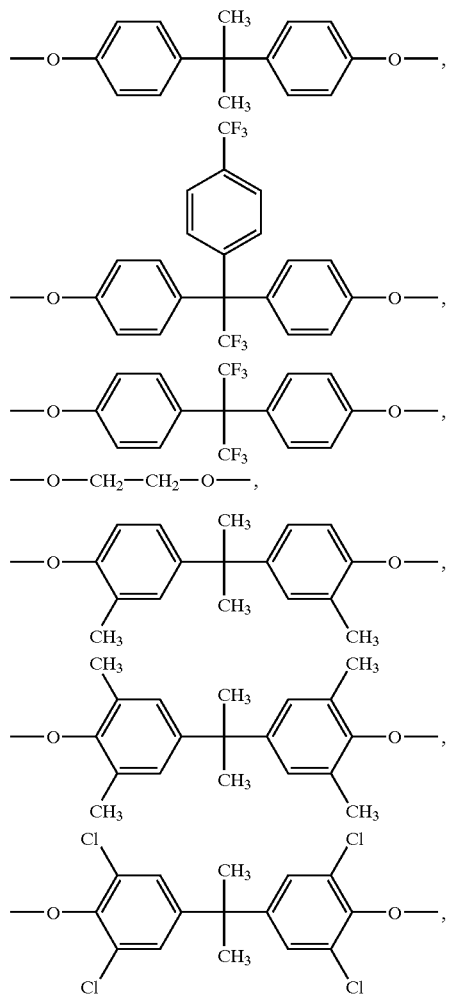

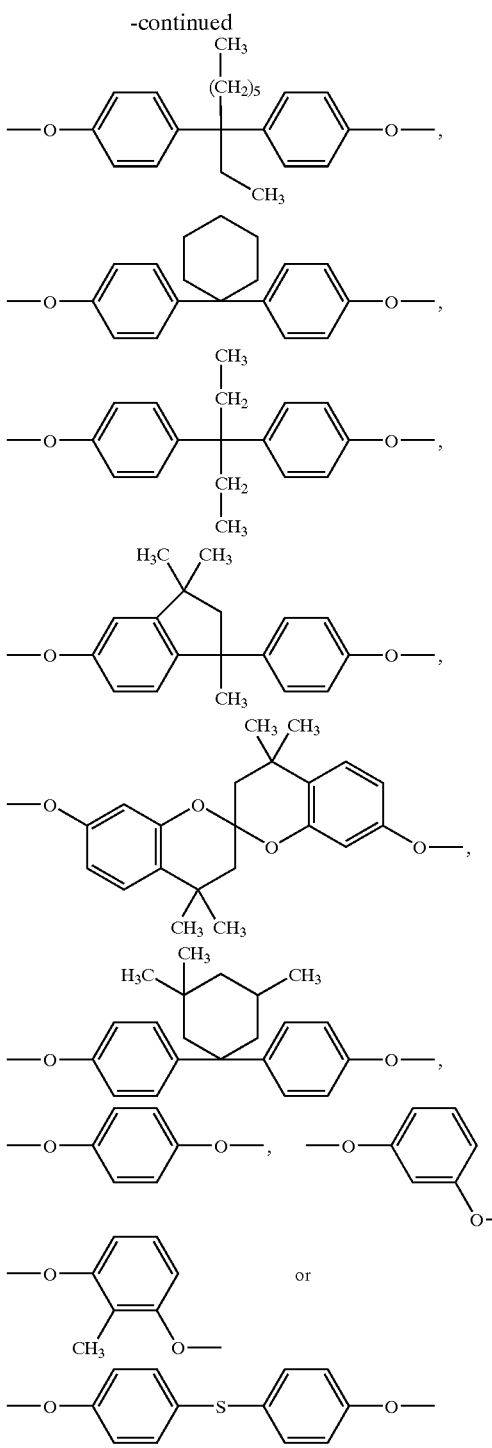

and also the corresponding dithio compounds ($T_1$ and $T_2$=S).

Also, the preferred B are those wherein W or A have the following meanings:

—CH$_2$—, —CH$_2$—CH$_2$—, —CH$_2$CH$_2$CH$_2$—,
—CH$_2$CH$_2$CH$_2$CH$_2$—,

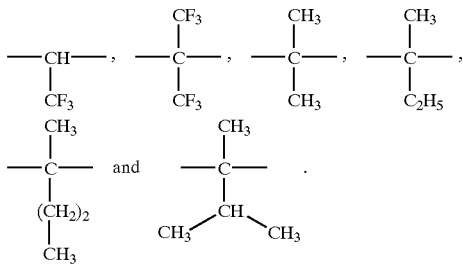

Very particular preference is given to compounds of the formula (II) where $Y_1=Y_2$
$R_{a1}=R_{a2}$
$R_{b1}=R_{b2}$ and
$Ar_1=Ar_2$.

Preference is also given to compounds of the formula (IIa) where n=m,
$R_1=R_2$,
$R_{a1}=R_{a2}$,
$R_{b1}=R_{b2}$,
o=p and
$R_3=R_4$, where in particular n, m, o and p are each 0.

Particular preference is given to compounds of the formula (II) which conform to the formula (IIb) or tautomeric forms thereof

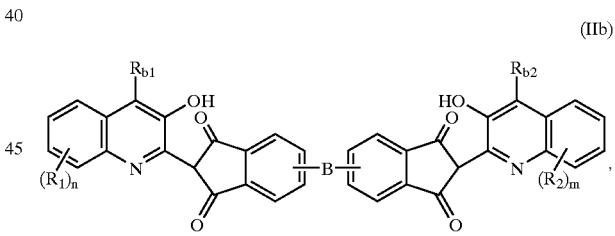

where n, m, $R_1$, $R_2$, $R_{b1}$, $R_{b2}$ and B are each as defined above.

The compounds of the formula (I) according to the invention are notable for excellent sublimation fastness in the mass coloration of plastics. They also possess very good light fastness, good thermal stability and particularly high colour strength. A colour strength comparison of for example the compounds of formula (II) with the non-doubled quinophthalones shows a disproportionately large increase (based on molecular weight increase).

When the quinophthalones of the formula (II) according to the invention have different meanings for $Y_1$ and $Y_2$ and/or $R_{a1}$ and $R_{a2}$, and/or $Ar_1$ and $Ar_2$, it can be advantageous to use any as-synthesized mixtures of symmetrical and asymmetrical quinophthalones.

Preference is likewise given to compounds of the formula (I) which conform to the formula (III) or tautomeric forms thereof

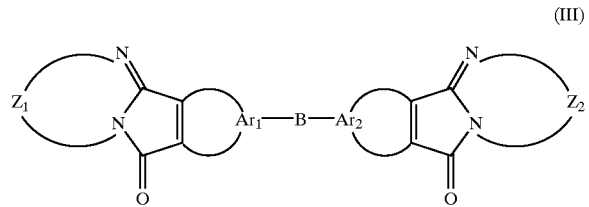
(III)

where $Z_1$ and $Z_2$ are independently optionally substituted ortho-phenylene, ortho-naphthylene, peri-(1,8)-naphthylene or arylene composed of more than two fused-together benzene rings, the aryl radicals which have more than two fused-together benzene rings being bridged ortho or in a manner corresponding to a peri position in naphthalene, and $Ar_1$, $Ar_2$ and B are each as defined above.

Possible substituents for the radicals $Z_1$ and $Z_2$ include for example the substituents mentioned for the radical Z.

Particularly preferred radicals $Z_1$ and $Z_2$ independently correspond to an optionally substituted peri-(1,8)-naphthylene.

Particular preference is given to compounds of the formula (III), which conform to the formula (IIIa)

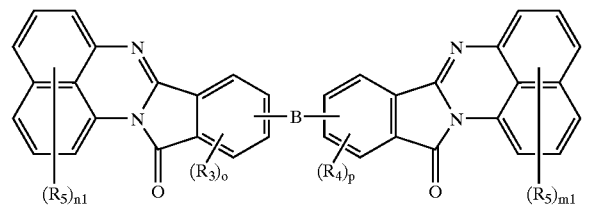
(IIIa)

where $n_1$ and $m_1$ are independently from 0 to 4,
$R_5$ and $R_6$ are each independently the same or different and can be the substituents mentioned for the radicals $Z_1$ and $Z_2$, especially halogen or $C_1$–$C_6$-alkyl,
o and p are independently from 0 to 2, especially 0 or 1,
$R_3$ and $R_4$ are each independently the same or different and can be the substituents mentioned for the radicals $Z_1$ and $Z_2$, especially halogen, $NO_2$, —NH-acyl or —NH-alkyl, and
B is as defined above. The preferred meaning of B corresponds to that indicated above.

Very particular preference is given to compounds of the formula (III)
wherein $Z_1=Z_2$ and
$Ar_1=Ar_2$.

Of corresponding advantage are compounds of the formula (IIIa)
wherein $n_1=m_1$,
$R_5=R_6$,
o=p and
$R_3=R_4$, where in particular $n_1$, $m_1$, o and p are each 0.

Particular preference is given to compounds of the formula (III) which conform to the formula (IIIb) or (IIIc)

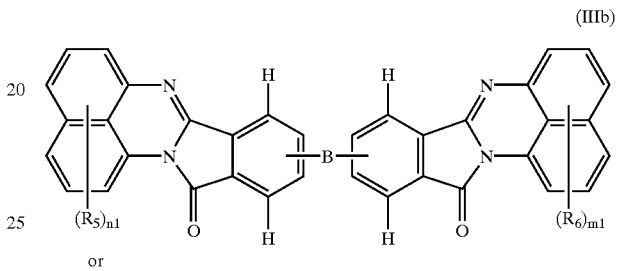
(IIIb)

or

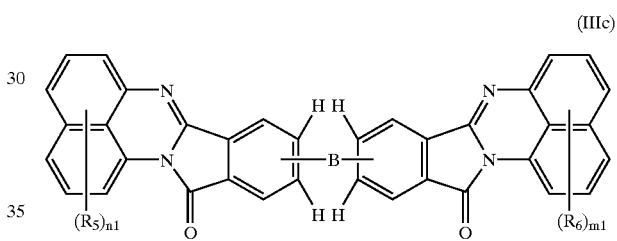
(IIIc)

where $n_1$, $m_1$, $R_5$, $R_6$ and B are each as defined above.

The compounds of the formula (III) according to the invention are likewise notable for excellent sublimation fastness in the mass coloration of plastics. They also possess very good light fastness, very good thermal stability and a particularly high color strength.

When the perinones of the formula (III) according to the invention have different meanings for $Z_1$ and $Z_2$ and/or for $Ar_1$ and $Ar_2$, it can be advantageous to use any as-synthesized mixtures of symmetrical and asymmetrical perinones of the formula (III).

Preference is likewise given to compounds of the formula (I) which conform to the formula (IV) or tautomeric forms thereof

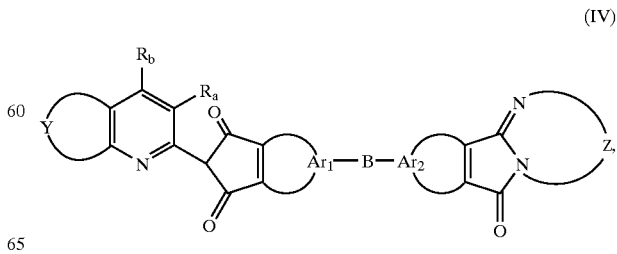
(IV)

where

Y, Z, $R_a$, $R_b$, $Ar_1$, $Ar_2$ and B are each as defined above.

Particular preference is given to compounds of the formula (IV) which conform to the formula (IVa) or tautomeric forms thereof

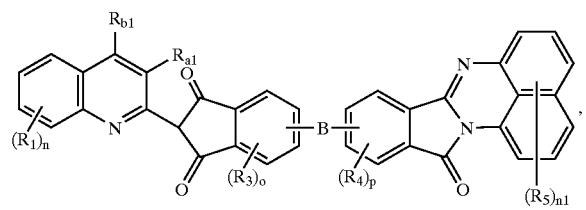
(IVa)

where $R_1$, $R_3$, $R_4$, $R_5$, $R_{b1}$, $R_{a1}$, B, n, p and $n_1$ are each as defined above.

Very particular preference is given to compounds of the formula (IV) which conform to the formula (IVb) or tautomeric forms thereof

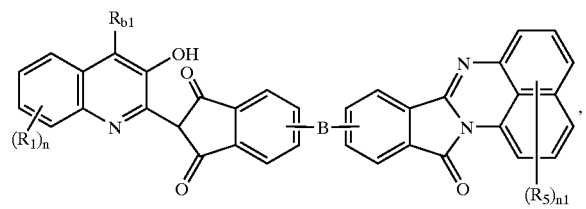
(IVb)

where $R_1$, $R_5$, $R_{b1}$, B, n and $n_1$ are each as defined above.

The compounds of the formula (IV) according to the invention are likewise notable for excellent sublimation fastness in the mass coloration of plastics. They also possess very good light fastness, good thermal stability and a particularly high colour strength.

Thermal stability is very good at temperatures as high as 300° C. and distinctly higher.

Particular preference is given to as-synthesized mixtures containing compounds of the formula (IV) and those of the formulae (II) and (III). Of advantage are in particular those mixtures which as well as the compound of the formula (IV) contain 0 to 25% by weight of a compound of the formula (II) and 0 to 25% by weight of a compound of the formula (III), the sum total of the compounds (IV), (II) and (III) being 100%.

Compounds of the formula (V) are described for example in Plaste und Kautschuk, Volume 28, No. 11/1981, p. 601–606.

The invention further provides a process for preparing the compounds of the formula (I) according to the invention, characterized in that tetracarboxylic acids or anhydrides of the formula (V)

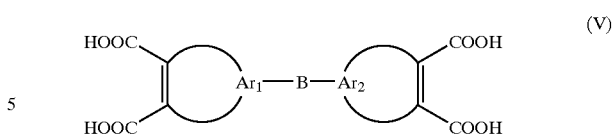
(V)

where $Ar_1$, $Ar_2$ and B are each as defined above, are condensed with one or more compounds of the formulae (VI) and/or (VII)

(VI)

(VII)

where $R_c$ is H, COOH or halogen, especially F, Br and Cl, especially H or COOH, and
Y, Z and $R_a$ are each as defined above, the sum total of the compounds of the formulae (VI) and (VII) being equal to two mole equivalents, based on tetracarboxylic acid (V).

The stated mole equivalents of the reactants employed for preparing the compound (I) merely serve to indicate the stoichiometry and do not preclude larger or smaller amounts which may be industrially more appropriate.

It will be appreciated that the employed compounds of the formulae (VI) and (VII) can also total more than two mole equivalents, based on tetracarboxylic acid (IV) or anhydrides thereof. However, it is preferable to use stoichiometric amounts.

The condensation reaction can be carried out directly by melting together equimolar amounts of the components of the formulae (V) and (VI) or (VII) at a temperature of 120° C. to 250° C. or more advantageously by reaction in a solvent at a temperature of 110° C. to 220° C., if appropriate under pressure, it being possible for the water of reaction to be removed by distillation.

Suitable solvents include for example: chlorobenzene, o-dichlorobenzene, trichlorobenzene, xylene, dimethylformamide, N-methylpyrrolidone glacial acetic acid, propionic acid, phenol, cresols, phenoxyethanol, glycols and mono- and dialkyl ethers thereof, alcohols, e.g., methanol, ethanol, i-propanol, n-butanol and water.

If appropriate, the reaction can be carried out in the presence of an acidic catalyst such as, for example: zinc chloride, p-toluenesulphonic acid, hydrochloric acid, sulphuric acid, organic acids, etc.

Particular preference is given to using the tetracarboxylic acid of the formula (V) in the form of its anhydride.

Preference is given to using in the process according to the invention compounds of the formula (V) which conform to the formula (Va) or anhydrides thereof

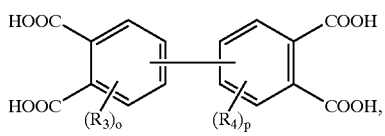

where $R_3$, $R_4$, B, o and p are each as defined above.

Very particular preference is given to using compounds of the formula (V) which conform to the formula (Vb) or the formula (Vc) or respective anhydrides thereof

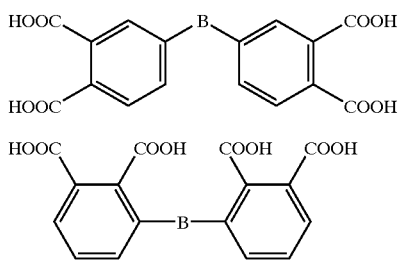

where

B is as defined above.

Preferred compounds of the formula (VI) are quinaldines of the formula (VIa)

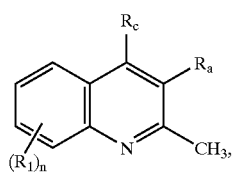

where $R_1$, $R_c$, $R_a$ and n are each as defined above.

Suitable quinaldines of the formula (VIa) are for example those of the hereinbelow mentioned formulae:

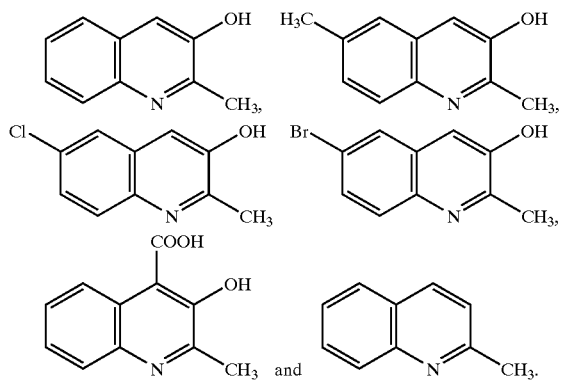

The diamines of the formula (VII) are known or can be prepared for example similarly to known diamines.

Preferred aromatic diamines of the formula (VII) are: o-phenylenediamine, chloro-o-phenylenediamines, dichloro-o-phenylenediamines, methyl-o-phenylenediamines, ethyl-o-phenylenediamines, methoxy-o-phenylenediamines, acetamino-o-phenylenediamines, phenyl-o-phenylenediamines, naphthylene-o-diamines, also 1,8-naphthylenediamine, chloro-1,8-naphthylenediamines, dichloro-1,8-naphthylenediamines, methyl-1,8-naphthylenediamines, dimethyl-1,8-naphthylenediamines, methoxy-1,8-naphthylenediamines, ethoxy-1,8-naphthylenediamines, acetamino-1,8-naphthylenediamines and 1,8-diaminoacetnaphthylene.

In a further preferred process variant, the compound of the formula (VII) is an optionally substituted peri-naphthylenediamine, especially 1,8-naphthylenediamine.

Preference is given to the novel process for preparing compounds of the formula (I) which conform to the formula (II), this process being characterized in that tetracarboxylic acids or anhydrides of the formula (V) are condensed with compounds of the formulae (VIb) and/or (VIc)

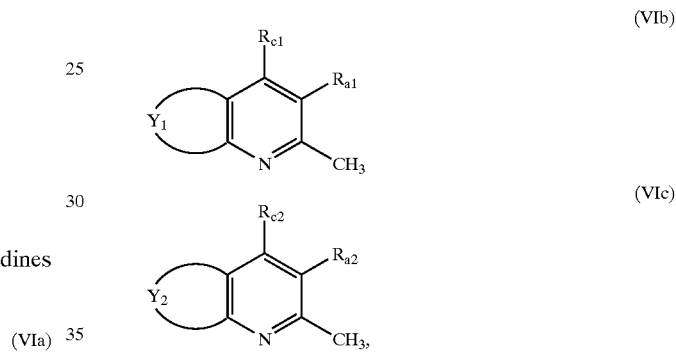

where $R_{c1}$ and $R_{c2}$ are independently H, COOH or halogen, especially F, Br or Cl, especially H or COOH, and $R_{a1}$, $R_{a2}$, $Y_1$ and $Y_2$ are each as defined above, the sum total of the compounds (VIb) and (VIc) being two mole equivalents, based on tetracarboxylic acid (V).

The condensation reaction can be carried out directly by melting together equimolar amounts of the components of the formulae (V) and (VIb) or (VIc) at a temperature of 160° C. to 250° C., preferably 180° C. to 220° C., more preferably 190 to 200° C., or more advantageously by reaction in a solvent at a temperature of 110° C. to 220° C. and preferably 160 to 180° C., if appropriate under pressure, it being possible for the water of reaction to be removed by distillation.

Preferred compounds of the formula (VIb) or (VIc) are quinaldines of the formula (VIbb)

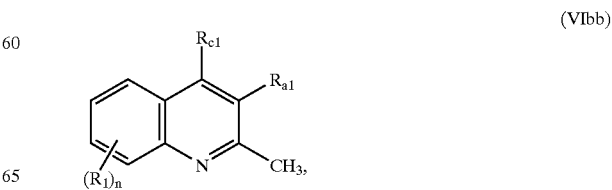

or of the formula (VIcc)

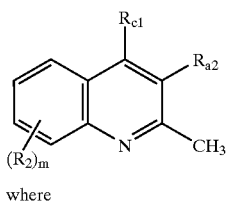

(VIcc)

where where $R_1$, $R_2$, $R_{c1}$, $R_{c2}$, $R_{a1}$, $R_{a2}$, n and m are each as defined above.

A reaction batch for preparing the compounds of the formula (II) is preferably worked up by dilution with alcohols such as methanol, ethanol, propanol or butanol. It is similarly possible to use aromatic diluents such as chlorobenzene or toluene and also ligroin. This process according to the invention preferably gives the compound according to the invention in yields of 85 to 95% of theory.

If appropriate, the condensation reaction can be followed by a halogenation reaction, especially a chlorination or bromination reaction, in which case this halogenation reaction is carried out under conditions known per se. For instance, the bromination of compounds of the formula (II) where $R_{b1}=R_{b2}=H$ in glacial acetic acid at a temperature of 80 to 120° C. leads to compounds of the formula (II), where $R_{b1}$ and $R_{b2}$ are each bromine.

The process according to the invention is likewise preferable for preparing the compounds of the formula (I) which conform to the formula (III), and it is characterized in that tetracarboxylic acids or anhydrides of the formula (V) are condensed with compounds of the formulae (VIIa) and/or (VIIb)

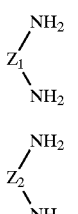

(VIIa)

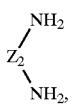

(VIIb)

the sum total of the diamines (VIIa) and (VIIb) used being two mole equivalents, based on tetracarboxylic acids (V), $Z_1$ and $Z_2$ each being as defined above.

The condensation reaction to prepare compounds of the formula (III) can be carried out directly by melting together equimolar amounts of the components of the formulae (V) and (VIIa) or (VIIb) at a temperature of 120° C. to 250° C., preferably at 120 to 180° C., or more advantageously by reaction in a solvent at a temperature of 80° C. to 220° C., preferably at 120 to 180° C., if appropriate under pressure, it being possible for the water of reaction to be removed by distillation.

Compounds of the formula (III) which optionally bear substituents from the group of the alkylaminosulphonyl and arylaminosulphonyl radicals are preparable for example from the corresponding compounds of the formula (III) in which one substituent is a chlorosulphonyl radical, using alkyl- or arylamines respectively.

Compounds of the formula (III) according to the invention in which one substituent is an aryloxysulphonyl radical can also be obtained by reaction of the corresponding chlorosulphonyl dyes with phenols or naphthols in the presence of a base, for example pyridine, triethylamine, alkali or alkaline earth metal carbonates, hydroxides or oxides.

Compounds of the formula (III) in which there are substituents representing alkyloxy or acyloxy can additionally be prepared by alkylation and acylation respectively of the compounds according to the invention which bear a hydroxyl group.

Those compounds of the formula (III) having an optionally acylated or alkylated amino group are also obtainable by reduction of the corresponding compounds in which the corresponding substituent is a nitro group using customary reducing agents, for example iron, zinc, sodium sulphide, hydrogen, etc, and if appropriate subsequent acylation or alkylation. The acylating step can also be carried out in the course of the reduction by adding an acylating agent.

The reaction batch for preparing compounds of the formula (III) is preferably worked up by dilution with alcohols such as methanol, ethanol, propanol or butanol. Similarly, aromatic diluents such as chlorobenzene or toluene and also ligroin can be used. The process according to the invention preferably gives the compounds according to the invention in yields of 90 to 95% of theory.

The process according to the invention is likewise preferable for preparing compounds of the formula (I) which conform to the formula (IV), the process being characterized in that tetracarboxylic acids or anhydrides of the formula (V) are condensed with compounds of the formula (VI) and diamines of the formula (VII), the substituents on the compounds mentioned having the above-mentioned meanings and the sum total of the compounds of the formulae (VI) and (VII) being two mole equivalents, based on tetracarboxylic acid (V). Preferred compounds of the formulae (V) to (VII) are those mentioned above.

The ratio of the compounds (VI) and (VII) to each other can vary within wide limits. It is for example (VI) to (VII)=10:90 to 90:10. The ratio is preferably about 1:1.

The condensation reaction can be carried out directly by melting together equimolar amounts of the components of the formulae (V) and (VI) and (VII) at a temperature of 160° C. to 250° C., preferably 180 to 220° C. and particularly preferably 190 to 200° C. or more advantageously in a solvent at a temperature of 110° C. to 220° C. and preferably 160 to 180° C., if appropriate under pressure, it being possible for the water of reaction to be removed by distillation.

The compounds of the formula (I) according to the invention are highly suitable for the mass coloration of plastics.

The term mass coloration as used herein comprehends in particular processes in which the dye is incorporated into the molten plastic material, for example with the aid of an extruder, or in which the dye is added to starting components for preparing the plastics, for example to monomers before the polymerization.

Particularly preferred plastics are thermoplastics, for example vinyl polymers, polyesters and polyamides.

Suitable vinyl polymers are polystyrene, styrene-acrylonitrile copolymers, styrene-butadiene copolymers, styrene-butadiene-acrylonitrile terpolymers, polymethacrylate, polyvinyl chloride, etc.

Polyesters which are further suitable are polyethylene terephthalates, polycarbonates and cellulose esters.

Preference is given to polystyrene, styrene interpolymers, polycarbonates and polymethacrylate. Particular preference is given to polystyrene.

The high molecular weight compounds mentioned can be present individually or in mixtures, as plastically deformable compositions or melts.

The dyes, according to the invention, are used in finely divided form, for which the use of dispersants is possible but not mandatory.

When the compounds (I) are used after polymerization, they are preferably mixed or ground dry with the polymer chips and this mixture is plastificated and homogenized, for example on mixing rolls or in screws, but the dyes can also be added to the liquid melt and homogeneously dispersed therein by stirring. The thus precolored material is then further processed as usual, for example by spinning, into bristles, filaments, etc or by extrusion or injection moulding into shaped articles.

Since the dyes of the formula (I) are stable to polymerization catalysts, especially peroxides, it is also possible to add the dyes to the monomeric starting materials for the plastics and then to polymerize in the presence of polymerization catalysts. To this end, the dyes are preferably dissolved in or intimately mixed with the monomeric components.

The dyes of the formula (I) according to the invention are particularly readily soluble in monomeric starting materials for plastics (e.g., methyl methacrylate).

The dyes of the formula (I) are preferably used for colouring the polymers mentioned in amounts from 0.0001 to 1% by weight and especially 0.01 to 0.5% by weight, based on the amount of polymer.

By adding pigments insoluble in the polymers, for example titanium dioxide, it is possible to obtain corresponding valuable hiding colorations.

Titanium dioxide can be used in an amount of 0.01 to 10% by weight and preferably 0.1 to 5% by weight, based on the amount of polymer.

The process according to the invention can also utilize mixtures of various dyes of the formula (I) and/or mixtures of dyes of the formula (I) with other dyes and/or inorganic or organic pigments.

The compounds of the formula (II) are yellow, and the compounds of the formula (III) and those of the formula (V) are orange.

The examples hereinbelow, in which parts and percentages are by weight, illustrate the invention.

EXAMPLES

Example 1

30 g of N-methyl-2-pyrrolidine (NMP) are admixed with 5.2 g (0.01 mol) of a bisphthalic anhydride of the formula

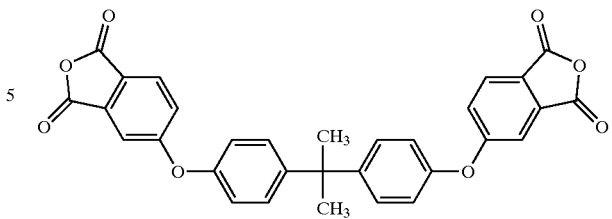

and 3.2 g (0.02 mol) of 1,8-naphthalenediamine of the formula

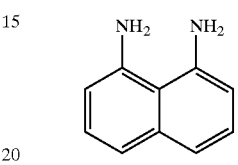

and heated to 120° C. with stirring. Stirring was continued at the reaction temperature for 4 hours. The reaction mixture was then cooled down to room temperature and was gradually admixed with 150 ml of methanol, the addition taking about 1 hour. The crystalline precipitate was filtered off with suction and repeatedly washed with methanol. This was followed by a wash with hot water and drying at 70° C. under reduced pressure.

Yield: 6.8 g (89%)

The dye has the formula

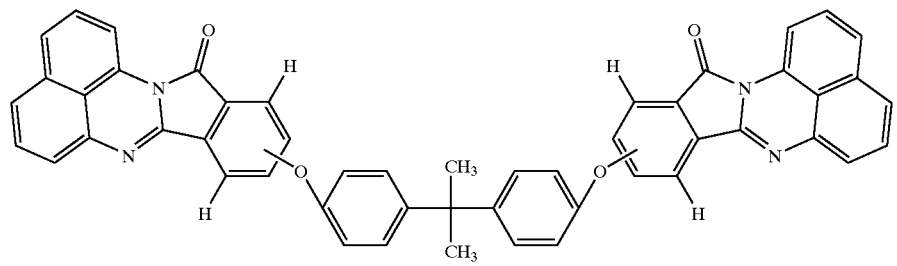

The dye colours plastics such as nylon 6, ABS, polyester and polystyrene in bright neutral orange shades having very good fastnesses and it is very readily soluble in the molten plastic at the processing temperatures required.

The synthesis was repeated using phenyl, o-dichlorobenzene, nitrobenzene and ditolyl ether instead of N-methylpyrrolidone (NMP) as solvent. Similar results were obtained.

Comparative Examples (a) Compared with the corresponding unbridged dye of the formula

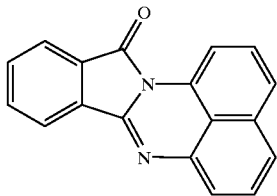

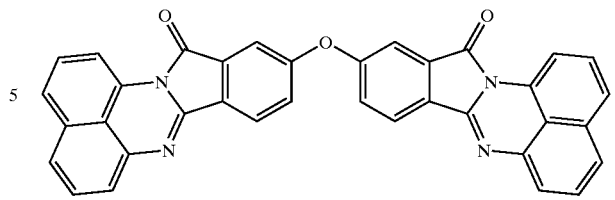

the sublimation fastness is distinctly improved. Whereas the unbridged dye shows distinct signs of sublimation at as low a temperature as 350° C. and completely sublimes on further heating to 450° C., the bridged dye possesses excellent sublimation fastness even at that temperature.

(b) The dye is very readily soluble in methyl methacrylate even at room temperature. In contradistinction, the bridged dye of the formula mentioned in Example 16 of EP-A-827 986 is virtually completely insoluble in MMA. The same is true of organic solvents, for example N-methyl-2-pyrrolidone, dimethylformamide, dichloromethane and acetone. (This is advantageous for the cleaning of machines used for plastics pigmentation.)

The dye is distinctly easier to process into molten N6, ABS, poly-styrene, polypropylene and polyethylene than the dye described in Example 16 of EP-A-827 986.

Examples 1c–1r

The following perinone dyes, prepared similarly as described above, from the corresponding bisphthalic anhydrides, have the same advantageous properties:

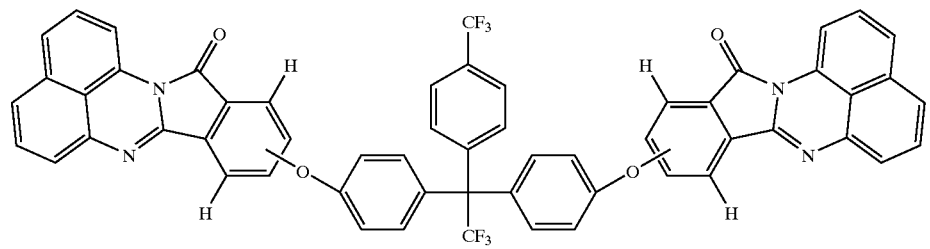

1c

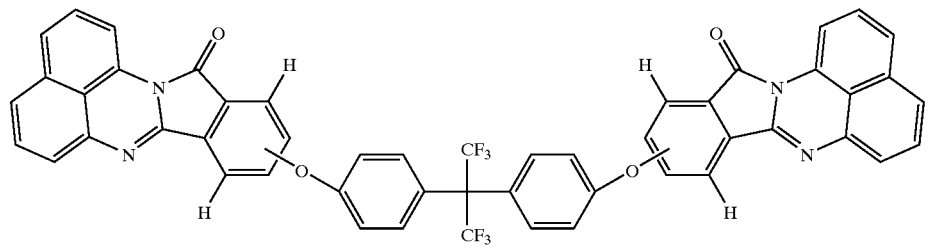

1d

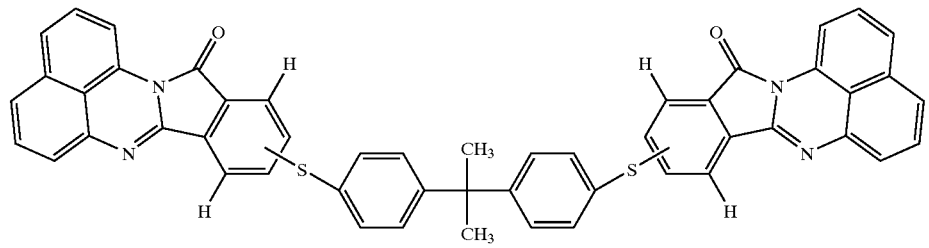

1e

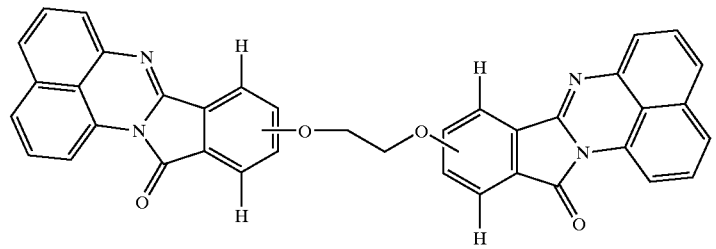

1f

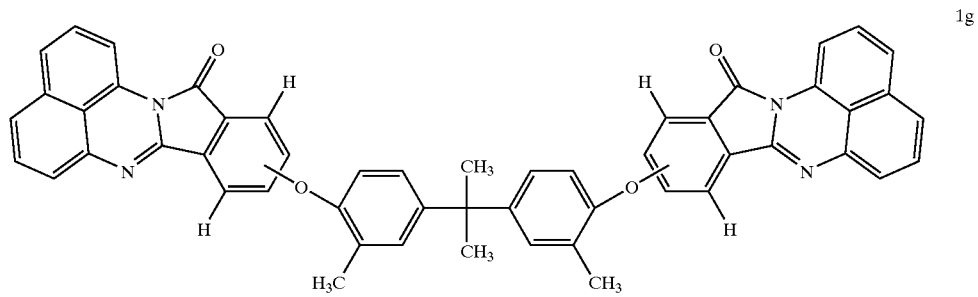
1g
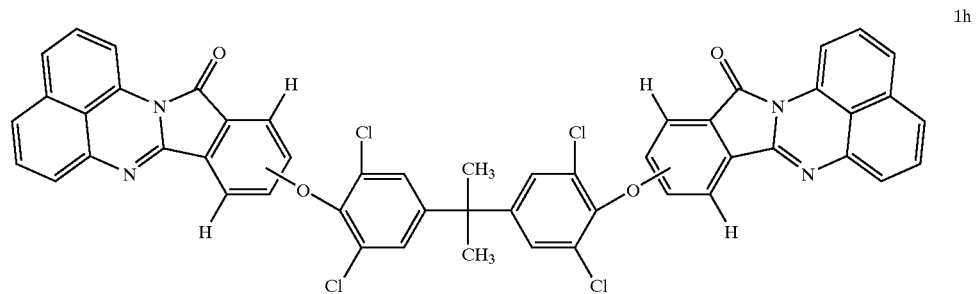
1h
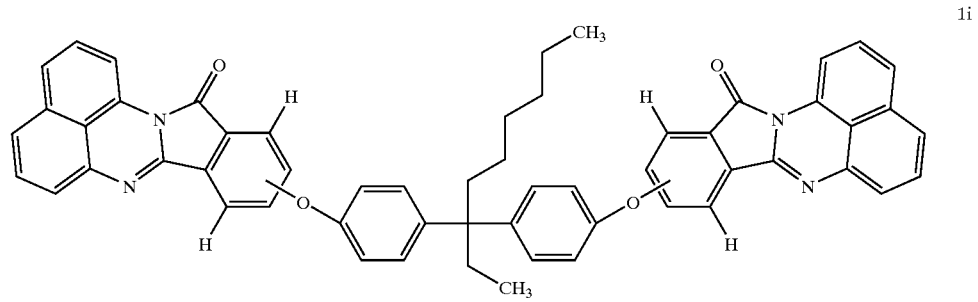
1i
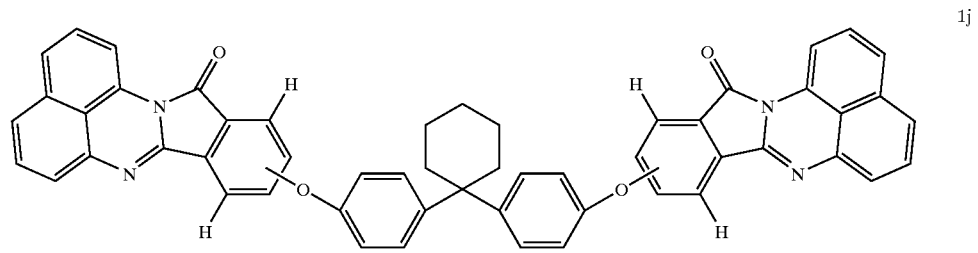
1j
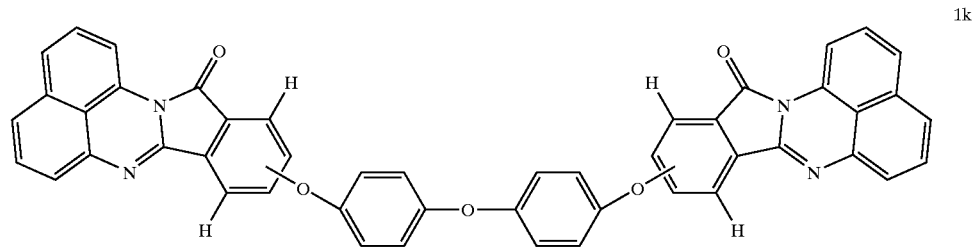
1k

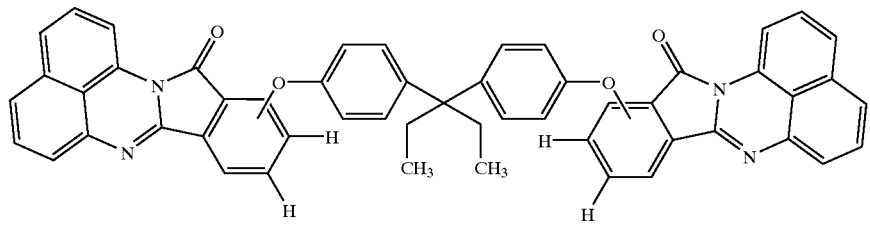
1l
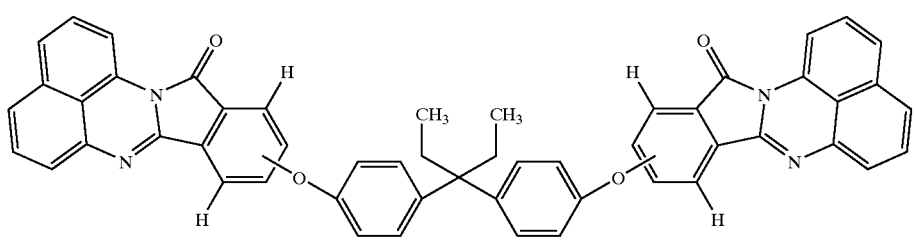
1m
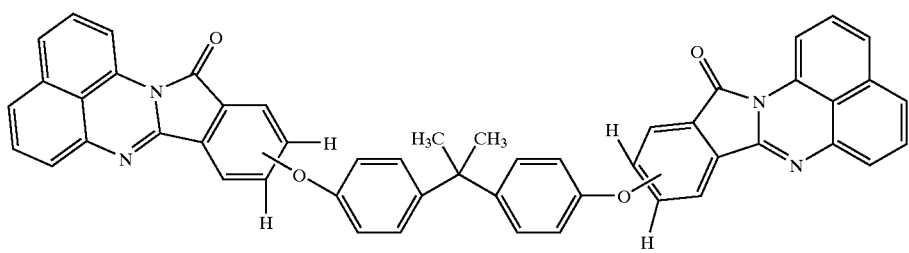
1n
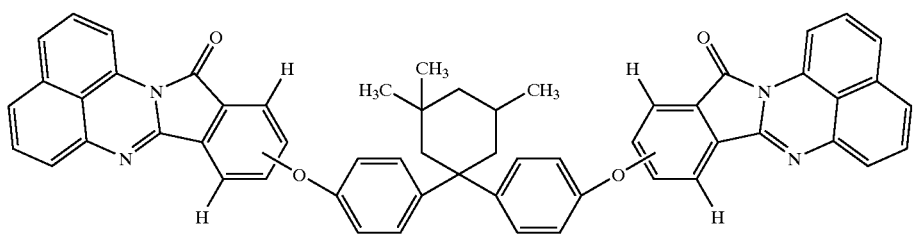
1o

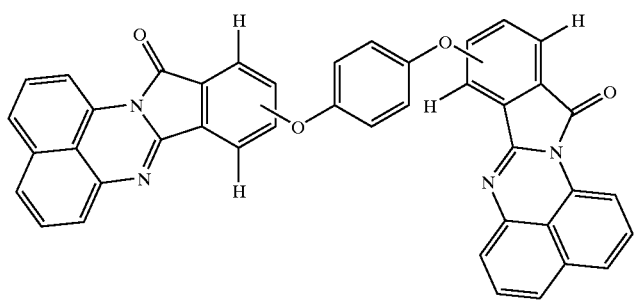

1p

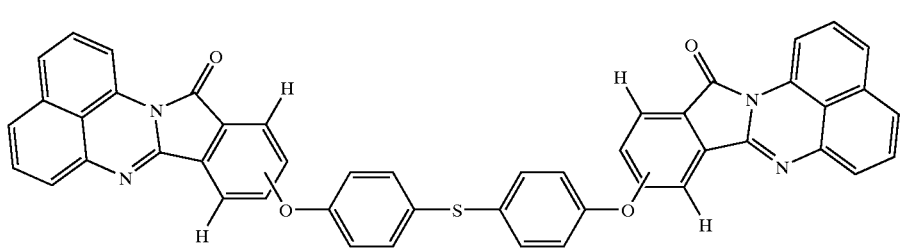

1q

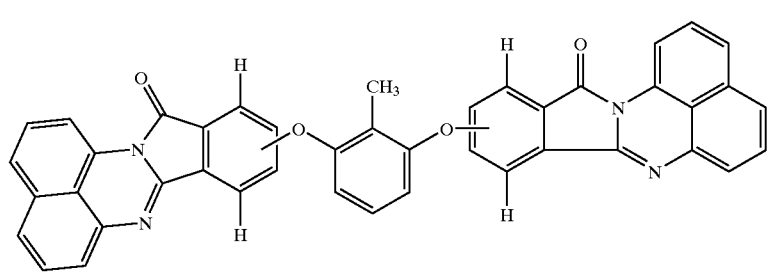

1r

Example 2

50 g of phenol were admixed at 70° C. with 5.2 g (0.010 mol) of a bisphthalic anhydride of the formula

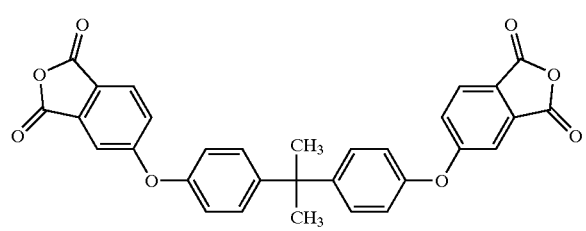

and 4.1 g (0.02 mol) of 3-hydroxyquinaldine-4-carboxylic acid of the formula

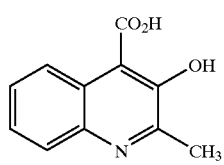

and heated to 175° C. with stirring. Stirring was continued at the reaction temperature for 12 hours, during which water of reaction was distilled off and carbon dioxide was eliminated from 3-hydroxyquinaldine-4-carboxylic acid. This was followed by cooling to 80° C. and gradual addition to the reaction mixture of 150 ml of methanol, adding over about 1 hour, during which the temperature initially decreased to 65 to 70° C. and was then maintained in this range. The crystalline precipitate was filtered off with suction and repeatedly washed with methanol. This was followed by a wash with hot water and drying at 70° C. under reduced pressure.

Yield: 7.2 g (90%)
The dye has the formula

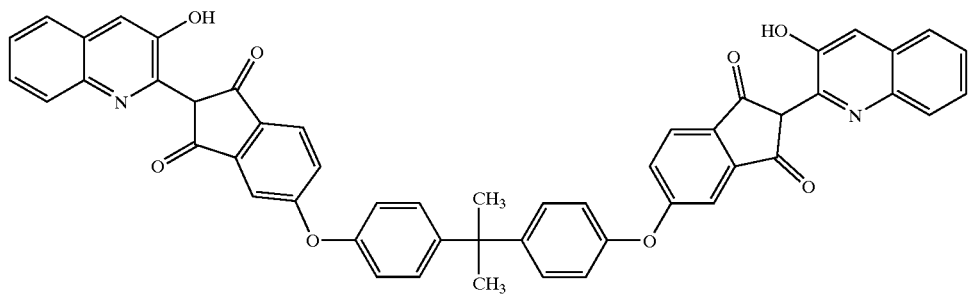

The preparation was repeated using o-dichlorobenzene, nitrobenzene, N-methyl-2-pyrrolidone (NMP) and ditolyl ether as solvent instead of phenol. Similar results were obtained.

The dye colours plastics such as ABS, polyester and polystyrene in bright neutral yellow shades having very good fastnesses.

Examples 2b–2d

The following quinophthalone dyes were prepared in a similar manner from the corresponding bisphthalic anhydrides:

All the dyes colour plastics such as ABS, polystyrene and polyester in bright yellows having very good fastnesses.

Example 3

47 g of phenol were admixed at 70° C. with 5.2 g (0.010 mol) of a bisphthalic anhydride of the formula

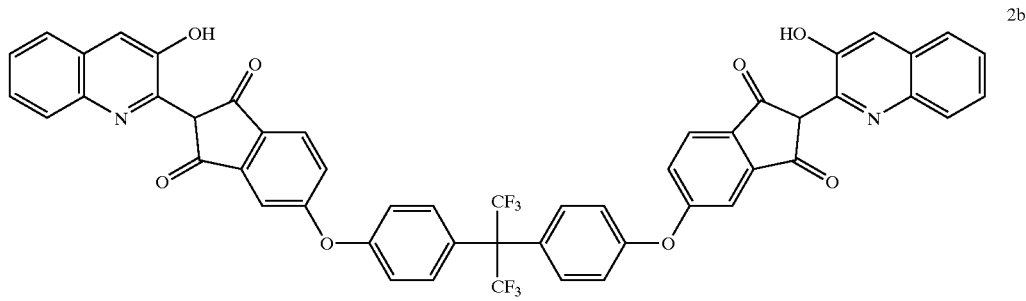

2b

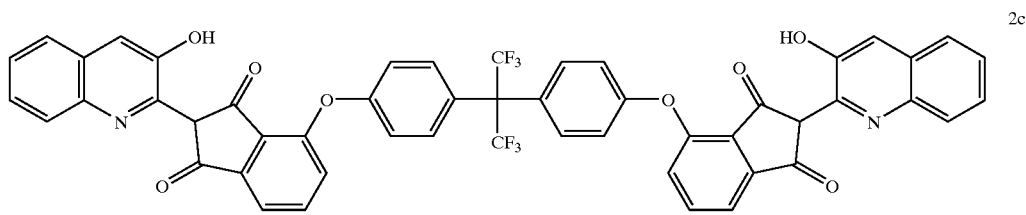

2c

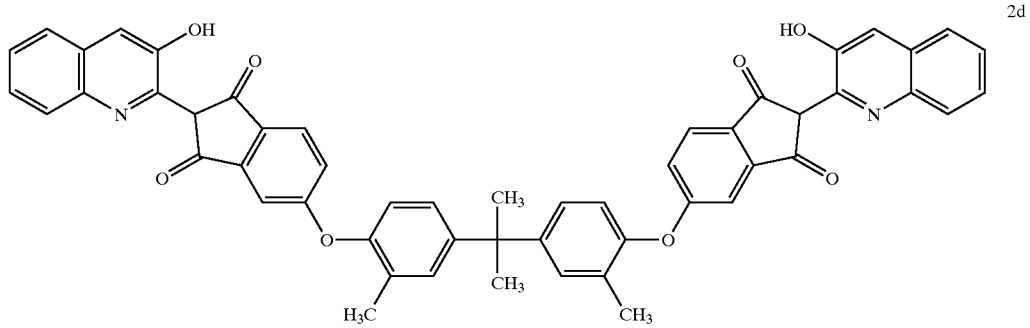

2d

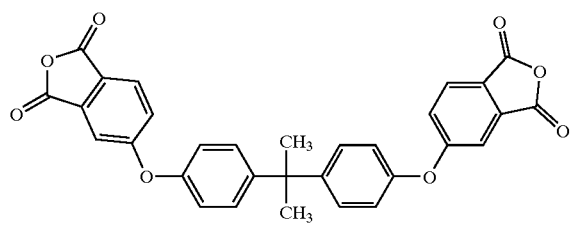

and 2.0 g (0.01 mol) of 3-hydroxyquinaldine-4-carboxylic acid and also 1.6 g (0.01 mol) of 1,8-naphthalenediamine and heated to 175° C. with stirring. Stirring was continued at reaction temperature for 12 hours, during which water of reaction was distilled off and carbon dioxide was eliminated from 3-hydroxyquinaldine-4-carboxylic acid. This was followed by cooling to 80° C. and gradual addition to the reaction mixture of 150 ml of methanol over about 1 hour, during which the temperature initially dropped to 65 to 70° C. and was then maintained in this range. The crystalline precipitate was filtered off with suction and repeatedly washed with methanol. This was followed by a wash with hot water and drying at 70° C. under reduced pressure.

Yield: 7.0 g (90%)

The dye has the formula and contains about 10% each of the symmetrical quinophthalone or perinone.

The reaction was repeated using o-dichlorobenzene, nitrobenzene, N-methyl-2-pyrrolidone (NMP) and ditolyl ether as solvent instead of phenol. Similar results were obtained.

The dye colours plastics such as ABS, polyester and polystyrene in bright orange shades having very good fastnesses.

Example 3a–3g

The following dyes were prepared in a similar manner from the corresponding bisphthalic anhydrides, diamines and quinaldines:

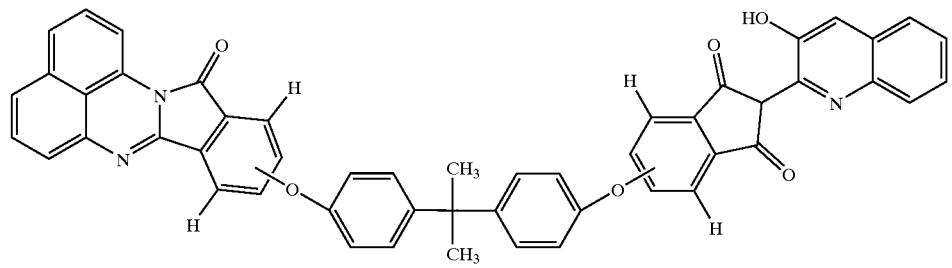

3b

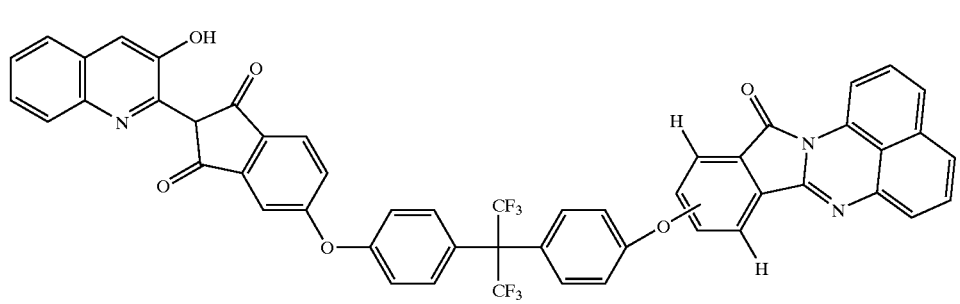

3c

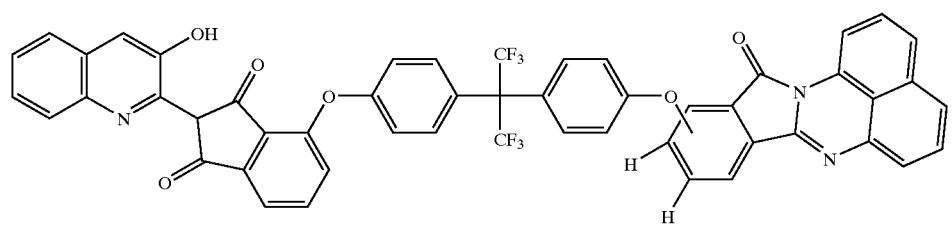

-continued

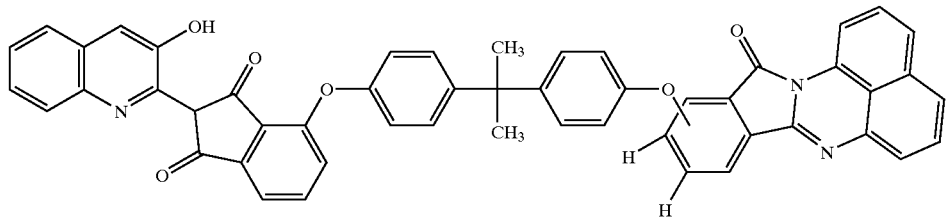

3d

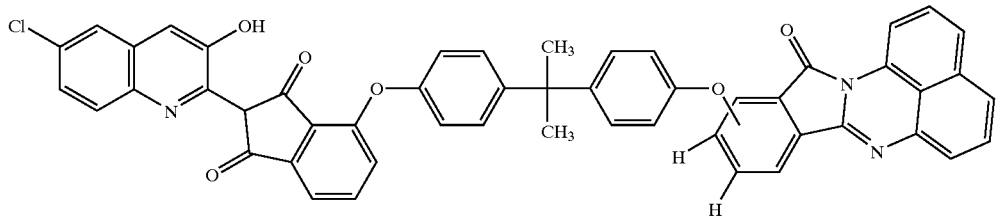

3e

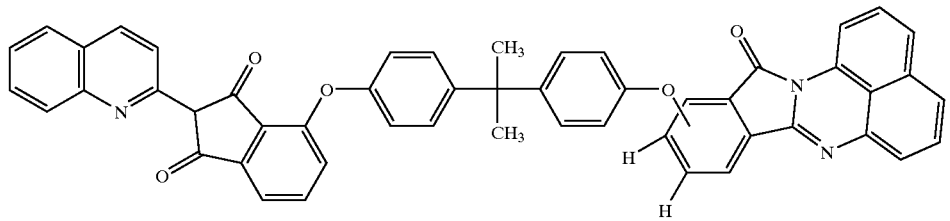

3f

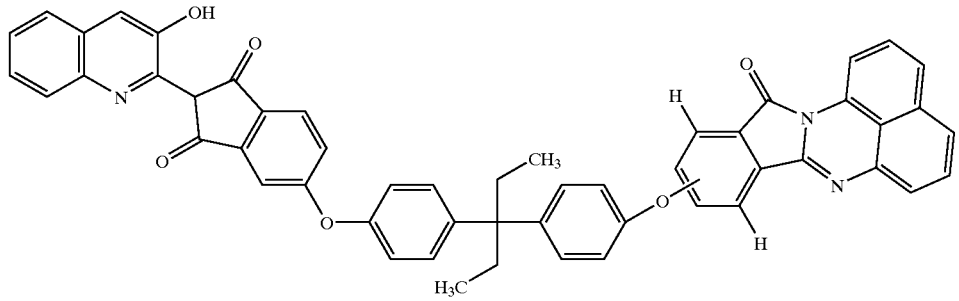

3g

All the dyes color plastics such as ABS, polystyrene and polyester in bright orange shades having very good fastnesses.

Example 4

47 g (0.5 mol) of phenol were admixed at 70° C. with 5.2 g (0.010 mol) of a bisphthalic anhydride of the formula

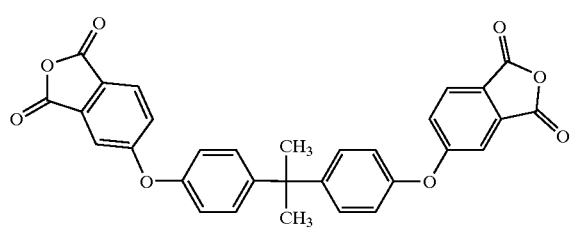

and 2.9 g (0.20 mol) of quinaldine of the formula

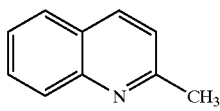

and heated to 175° C. with stirring. Stirring was continued at reaction temperature for 12 hours, during which water of reaction distilled off. The reaction mixture was then cooled to 80° C. and gradually admixed with 150 ml of methanol added over about 1 hour, during which the temperature initially dropped to 65 to 70° C. and was then maintained in this range. The crystalline precipitate was filtered off with suction and repeatedly washed with methanol. This was followed by a wash with hot water and drying at 70° C. under reduced pressure.

Yield: 7.2 g (93%)

The dye has the formula

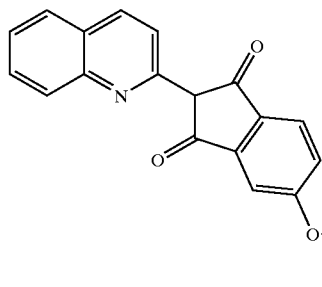

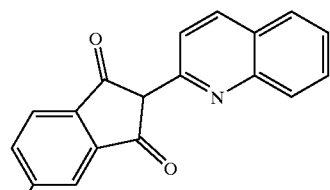

The preparation was repeated using o-dichlorobenzene, nitrobenzene, N-methyl-2-pyrrolidone (NMP) and ditolyl ether as solvent instead of phenol. Similar results were obtained.

The dye colors plastics such as ABS, polyester and polystyrene in bright greenish yellow shades having very good fastnesses.

Example 4a–4e

The following quinophthalone dyes were prepared in a similar manner from the corresponding bisphthalic anhydrides and the corresponding quinaldine derivatives:

4b

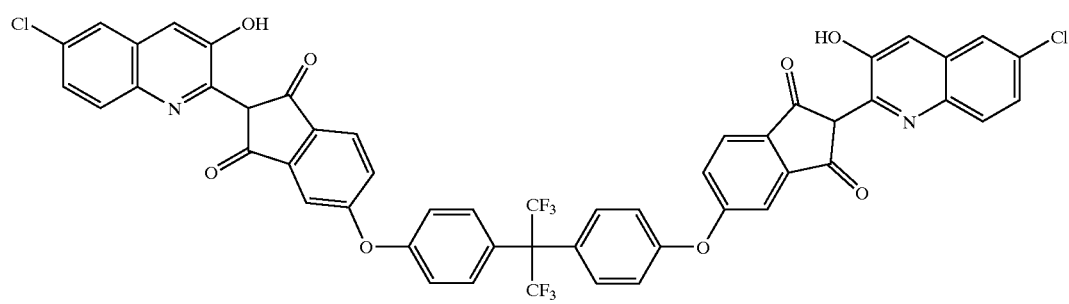

4c

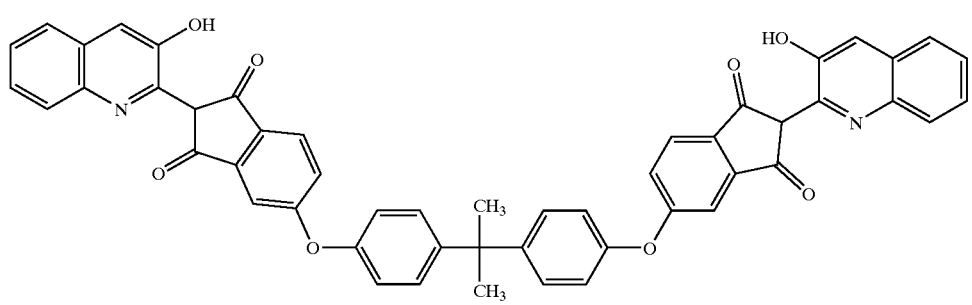

4d

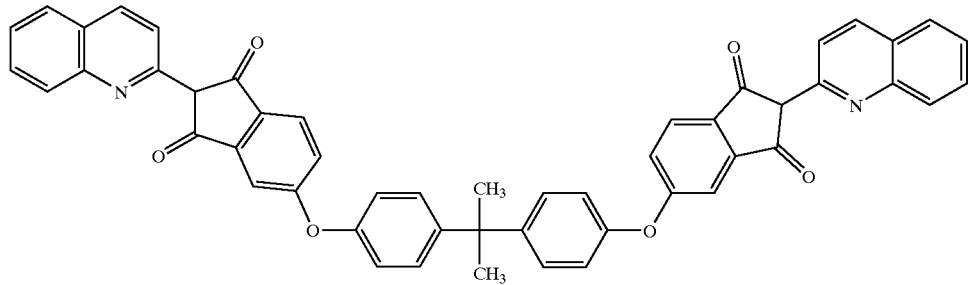

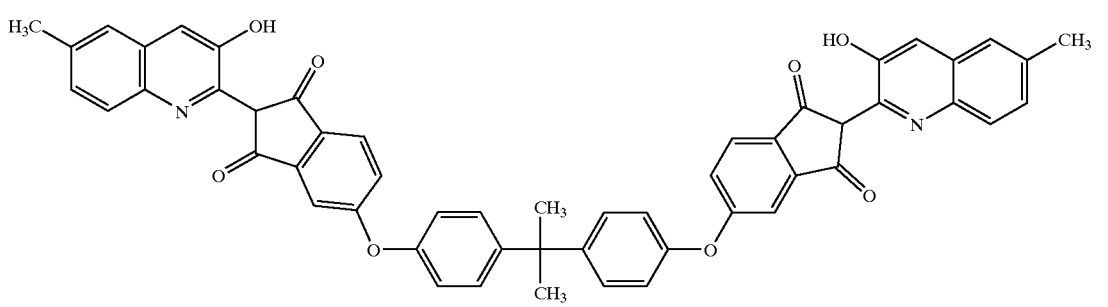

4e

Example 5

50 g (0.5 mol) of phenol were admixed at 70° C. with 5.2 g (0.010 mol) of a bisphthalic anhydride of the formula

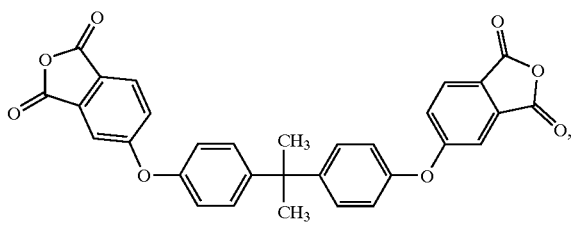

1.4 g (0.010 mol) of quinaldine of the formula

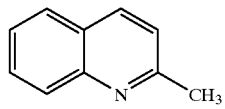

and heated to 175° C. with stirring. Stirring was continued at reaction temperature for 12 hours, during which water of reaction distilled off and carbon dioxide was eliminated from 3-hydroxyquinaldine-4-carboxylic acid. The reaction mixture was then cooled to 80° C. and gradually admixed with 150 ml of methanol over about 1 hour, during which the temperature initially dropped to 65 to 70° C. and was then maintained in this range. The crystalline precipitate was filtered off with suction and repeatedly washed with methanol. This was followed by a wash with hot water and drying at 70° C. under reduced pressure.

Yield: 7.2 g (90%)

The dye has the formula

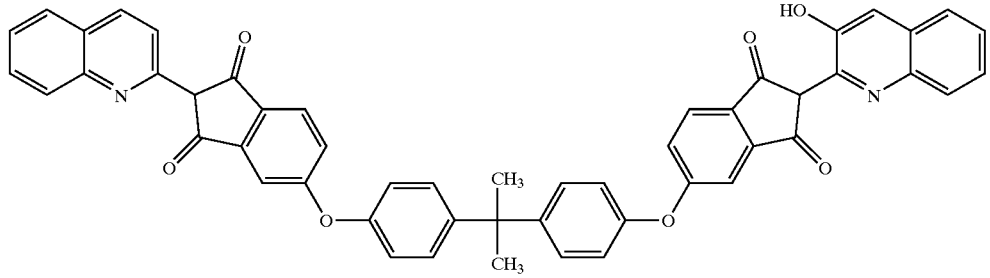

and 1.6 g (0.10 mol) of quinaldine of the formula

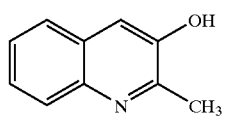

In addition, about 10% each of the two possible symmetrical dyes was obtained as well.

The preparation was repeated using o-dichlorobenzene, nitrobenzene, N-methyl-2-pyrrolidone (NMP) and ditolyl ether as solvent instead of phenol. Similar results were obtained.

The dye colours plastics such as ABS, polyester and polystyrene in bright yellow shades having very good fastnesses.

Example 5a–5

The following quinophthalone dyes were prepared in a similar manner from the corresponding bisphthalic anhydrides and the corresponding quinaldine derivatives:

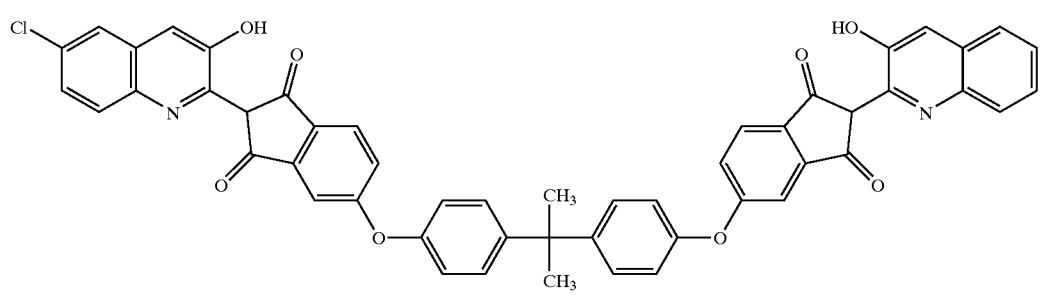

5b

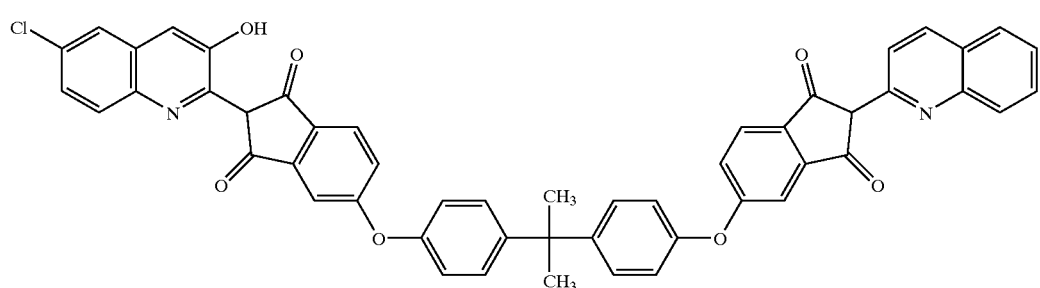

5c

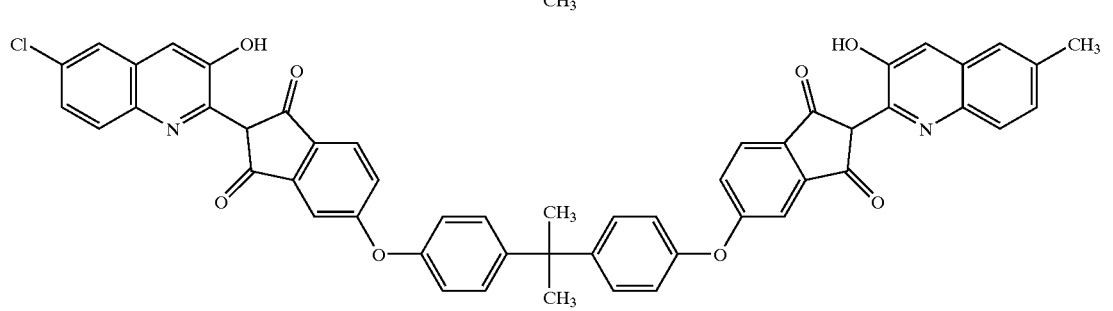

5d

Example 6

30 g of N-methyl-2-pyrrolidone (NMP) were admixed with 5.2 g (0.010 mol) of a bisphthalic anhydride of the formula

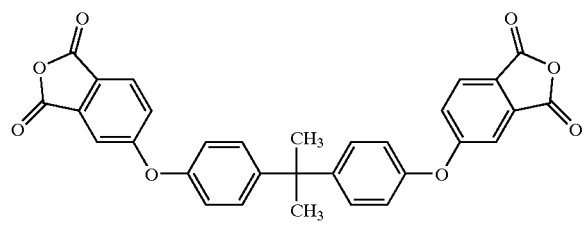

and 1.60 g (0.01 mol) of 1,8-naphthalenediamine of the formula

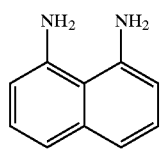

and 1.10 g (0.01 mol) of o-phenylenediamine of the formula

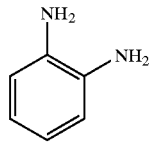

and heated to 120° C. with stirring. Stirring was continued at reaction temperature for 4 hours. The reaction mixture was then cooled to room temperature and gradually admixed with 150 ml of methanol over about 1 hour. The crystalline precipitate was filtered off with suction and repeatedly washed with methanol. This was followed by a wash with hot water and drying at 70° C. under reduced pressure.

Yield: 6.4 g (89%)
The dye has the formula

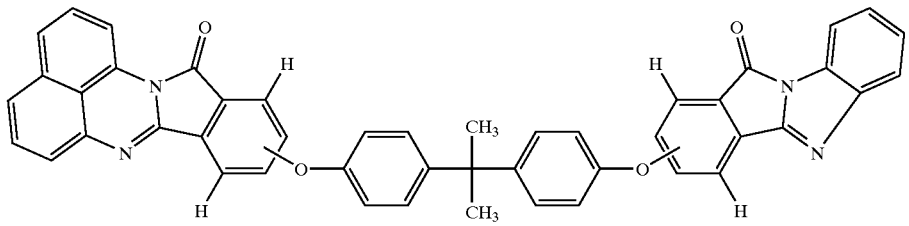
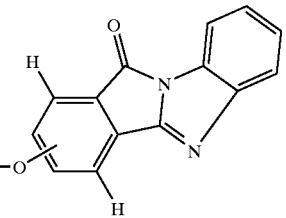

The dye colours plastics such as nylon 6, ABS, polyester and polystyrene in bright orange shades having very good fastnesses and is very readily soluble in the molten plastics at the required processing temperatures.

The synthesis was repeated using phenol, o-dichlorobenzene, nitrobenzene and ditolyl ether as solvent instead of NMP. Similar results were obtained.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Compounds of the formula (I) or tautomeric forms thereof

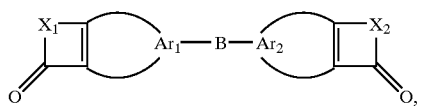

(I)

where

Ar$_1$ and Ar$_2$ are independently radicals needed to complete optionally substituted carbocyclic aromatics, B is a radical of the formula -T$_1$-W-T$_2$-, where T$_1$ and T$_2$ are independently O or S and W is alkylene, C$_6$–C$_{10}$-arylene, or cycloalkylene, which are each optionally substituted or is the radical of the formula (a)

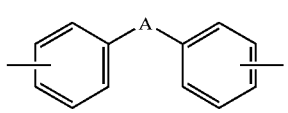

(a)

where the phenyl rings are optionally substituted and

A is a radical of the formula O, S, SO, SO$_2$ or CO, optionally substituted alkylene, or optionally substituted cycloalkylene, said alkylene or cycloalkylene being attached to the adjacent phenyl rings itself or via its substitutents, or W is a radical of the formulae —(CH$_2$)$_s$—O—(CH$_2$)$_t$—, —(CH$_2$)$_s$—S—(CH$_2$)$_t$—.

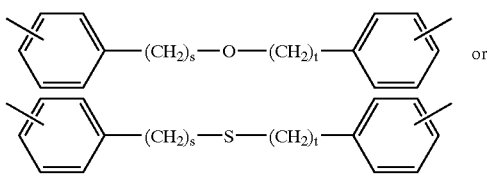

where s and t are independently from 1 to 6, the ends of the radical B each being attached to an aromatic carbon atom of the two radicals Ar$_1$ and Ar$_2$, and X$_1$ and X$_2$ are independently a radical of the formulae selected from the group consisting of

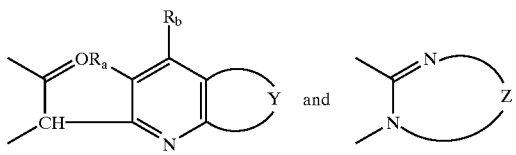

each being located in the ring in such a way that the

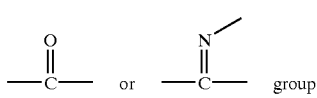

is adjacent to the C—C double bond, where

Y is the radical of an optionally substituted benzene or naphthalene ring,

Z is optionally substituted ortho-phenylene, ortho-naphthylene, peri-(1,8)-naphthylene or arylene comprising more than two fused-together benzene rings, aryl radicals which have more than two fused-together benzene rings being bridged ortho or in a manner corresponding to a peri position in naphthalene, R$_a$ is H or OH, and R$_b$ is H or halogen.

2. Compounds according to claim 1, wherein Ar$_1$ and Ar$_2$ are independently a radical needed to complete an optionally substituted benzene or naphthalene ring.

3. Compounds according to claim 2 wherein Ar$_1$ and Ar$_2$ are independently a radical needed to complete an optionally substituted benzene ring.

4. Compounds according to claim 1 wherein W is C$_1$–C$_6$-alkylene, or phenylene which is each optionally substituted.

5. Compounds according to claim 1 which conform to the formula (II) or tautomeric forms thereof (II)

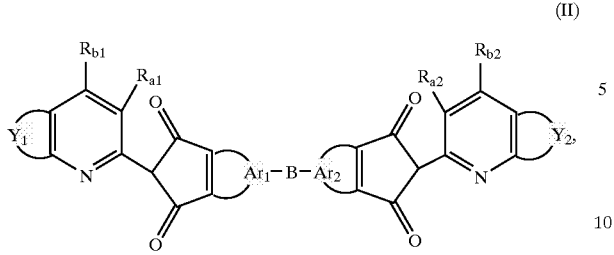

where

Y$_1$ and Y$_2$ are independently the radical of an optionally substituted benzene or naphthalene ring, R$_{a1}$ and R$_{a2}$ are independently H or OH, and R$_{b1}$ and R$_{b2}$ are independently H or halogen.

6. Compounds according to claim 5 which conform to the formula (IIa) or tautomeric forms thereof (IIa)

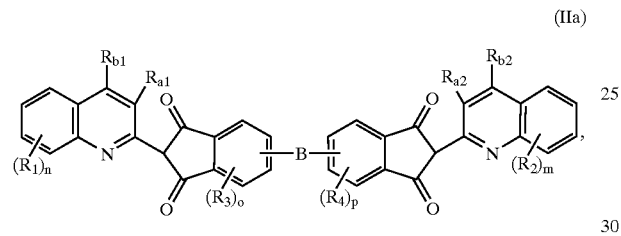

where n and m are independently from 0 to 4,

R$_1$ and R$_2$ are each independently the same or different and represent halogen, —COOH, —COOR, where R is C$_1$–C$_{10}$-alkyl, C$_6$–C$_{10}$-aryl or C$_5$–C$_8$-cycloalkyl, or are C$_1$–C$_6$-alkyl, o and p are independently from 0 to 2, especially 0 or 1, R$_3$ and R$_4$ are each independently the same or different and represent C$_1$–C$_6$-alkyl, halogen, alkylcarbonyl, arylcarbonyl, alkylsulphonyl, arylsulphonyl, nitro, aryl, aryloxysulphonyl, hydroxyl, C$_1$–C$_6$-alkoxy, or benzyloxy, aryloxy, optionally alkyl- or acyl-substituted amino optionally alkyl- or aryl-substituted aminosulphonyl, optionally alkyl-substituted carboxamide or a fused-on aromatic, cycloaliphatic or heterocyclic ring.

7. Compounds according to claim 6 wherein R$_1$ and R$_2$ are each independently the same or different and represent Cl or Br.

8. The compounds according to claim 6 wherein R is methyl or ethyl.

9. The compounds of claim 6 wherein o and p are independently 0 or 1.

10. Compounds of claim 6 wherein R$_3$ and R$_4$ are each independently the same or different and represent methyl, ethyl, n-propyl, iso-propyl, n-butyl, sec-butyl, tert-butyl, Cl and Br; optionally substituted phenyl or —SO$_2$OC$_6$H$_5$.

11. Compounds according to claim 1, wherein B is a radical of the formulae

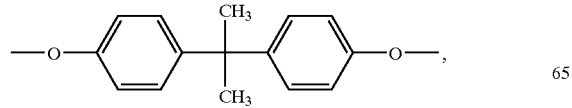

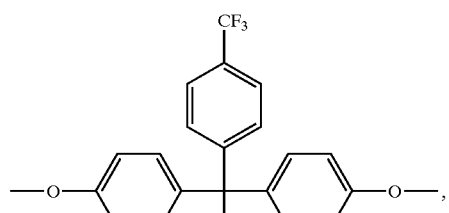

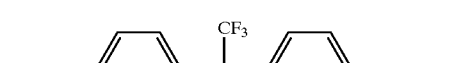

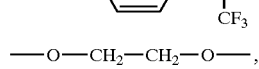

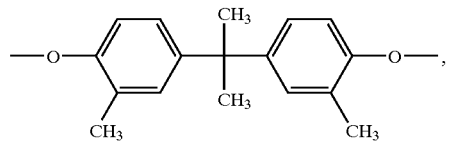

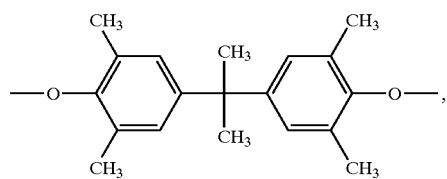

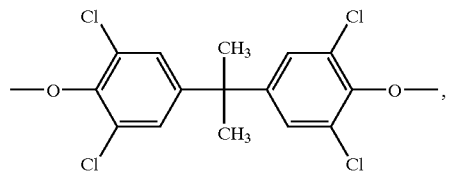

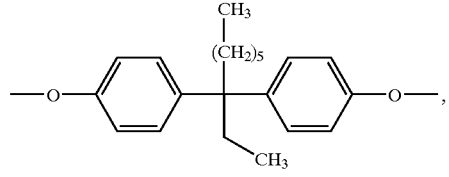

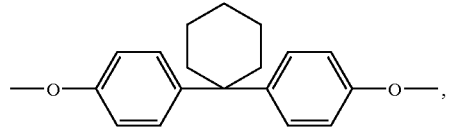

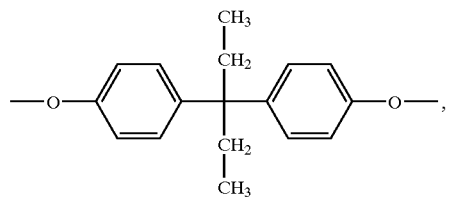

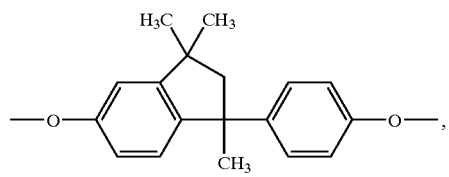

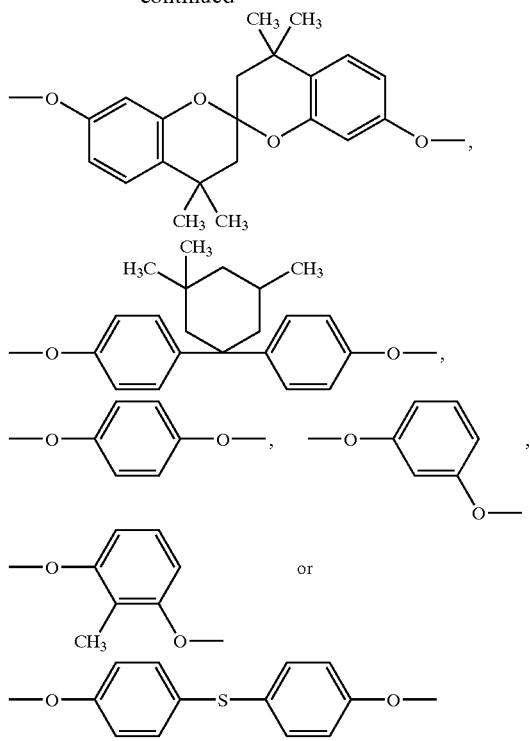

and also the corresponding dithio compounds wherein $T_1$ and $T_2$=S.

12. Compounds according to claim 5, wherein $Y_1=Y_2$,
$R_{a1}=R_{a2}$,
$R_{b1}=R_{b2}$ and
$Ar_1=Ar_2$.

13. Compounds according to claim 6, wherein n=m,
$R_1=R_2$,
$R_{a1}=R_{a2}$,
$R_{b1}=R_{b2}$,
o=p and
$R_3=R_4$ where
n, m, o and p are each 0.

14. Compounds according to claim 6 which conform to the formula (IIb) or tautomeric forms thereof

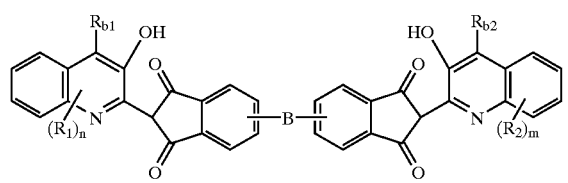

15. Compounds according to claim 1 which conform to the formula (III) or tautomeric forms thereof

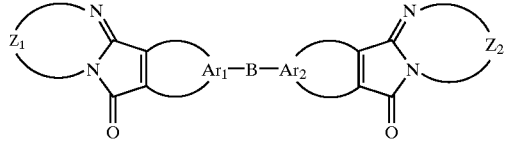

where
$Z_1$ and $Z_2$ are independently optionally substituted ortho-phenylene, ortho-naphthylene, peri-(1,8)-naphthylene or arylene composed of more than two fused-together benzene rings, aryl radicals which have more than two fused-together benzene rings being bridged ortho or in a manner corresponding to a peri position in naphthalene.

16. Compounds according to claim 15, wherein the radicals $Z_1$ and $Z_2$ are independently an optionally substituted peri-(1,8)-naphthylene.

17. Compounds according to claim 15 which conform to the formula (IIIa)

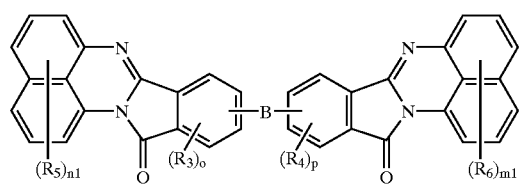

where
$n_1$ and $m_1$ are independently from 0 to 4,
$R_5$ and $R_6$ are each independently the same or different and represent $C_1$–$C_6$-alkyl, halogen, nitro, aryl, aryloxysulphonyl, hydroxyl, $C_1$–$C_6$-alkoxy, aryloxy, optionally alkyl- or acyl-substituted amino, optionally alkyl- or aryl-substituted aminosulphonyl, optionally alkyl-substituted carboxamide or a fused-on aromatic, cycloaliphatic or heterocyclic ring or $C_1$–$C_6$-alkyl,
o and p are independently from 0 to 2,
$R_3$ and $R_4$ are each independently the same or different and represent $C_1$–$C_6$-alkyl, halogen, nitro, aryl, aryloxysulphonyl, hydroxyl, $C_1$–$C_6$-alkoxy, aryloxy, optionally alkyl- or acyl-substituted amino, optionally alkyl- or aryl-substituted aminosulphonyl, optionally alkyl-substituted carboxamide or a fused-on aromatic, cycloaliphatic or heterocyclic ring, $NO_2$, —$NH_2$, —NH-acyl or —NH-alkyl.

18. Compounds according to claim 17 wherein $R_3$ and $R_4$ are each halogen.

19. Compounds of according to claim 17 wherein o and p are independently 0 or 1.

20. Compounds according to claim 15, where
$Z_1=Z_2$ and
$Ar_1=Ar_2$.

21. Compounds according to claim 17, where
$n_1=m_1$,
$R_5=R_6$,
o=p and
$R_3=R_4$
where
$n_1$, $m_1$, o and p are each 0.

22. Compounds according to claim 17 which conform to the formula (IIIb) or (IIIc)

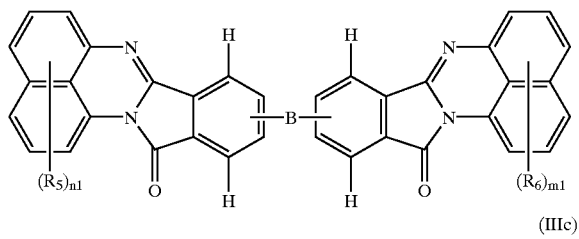

(IIIb)

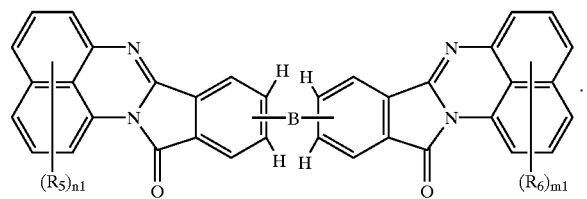

(IIIc)

23. Compounds according to claim 1 which conform to the formula (IV) or tautomeric forms thereof

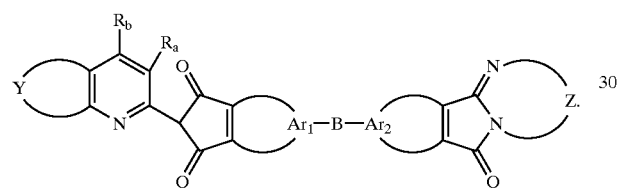

(IV)

24. Compounds according to claim 23 which conform to the formula (IVa) or tautomeric forms thereof

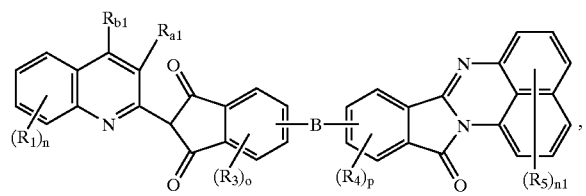

(IVa)

where
$R_{a1}$ is H or OH,
$R_{b1}$ is H or halogen,
n and $n_1$ are independently from 0 to 4,
each $R_1$ is halogen, —COOH, —COOR, where R is $C_1$–$C_{10}$-alkyl, $C_6$–$C_{10}$-aryl or $C_5$–$C_8$-cycloalkyl, or is $C_1$–$C_6$-alkyl
o and p are independently from 0 to 2,
$R_3$ and $R_4$ are each independently the same or different and represent $C_1$–$C_6$-alkyl, halogen, alkylcarbonyl, arylcarbonyl, alkylsulphonyl, arylsulphonyl, nitro, aryl, optionally substituted phenyl, aryloxysulphonyl, hydroxyl, $C_1$–$C_6$ alkoxy, aryloxy, optionally alkyl- or acyl-substituted amino, optionally alkyl- or aryl-substituted aminosulphonyl, optionally alkyl-substituted carboxamide or a fused-on aromatic, cycloaliphatic or heterocyclic ring, and
each $R_5$ is $C_1$–$C_6$-alkyl, halogen, nitro, aryl, aryloxysulphonyl, hydroxyl, $C_1$–$C_6$-alkoxy, aryloxy, optionally alkyl- or acyl-substituted amino, optionally alkyl- or aryl-substituted aminosulphonyl, optionally alkyl-substituted carboxamide or a fused-on aromatic, cycloaliphatic or heterocyclic ring.

25. Compounds according to claim 24 wherein $R_1$ is Cl or Br.

26. Compounds according to claim 24 wherein R is methyl or ethyl.

27. Compounds according to claim 24 wherein $R_3$ and $R_4$ are each independently the same or different and represent methyl, ethyl, n propyl, isopropyl, n butyl, sec butyl, tert butyl, Cl and Br; optionally substituted phenyl, —$SO_2OC_6H_5$, methoxy, benzyloxy; phenoxy, $NH_2$, $NHCOCH_3$, —$N(C_2H_5)_2$, $SO_2N(CH_3)_2$ or $SO_2NHCH_3$.

28. Compounds according to claim 24 which conform to the formula (IVb) or tautomeric forms thereof

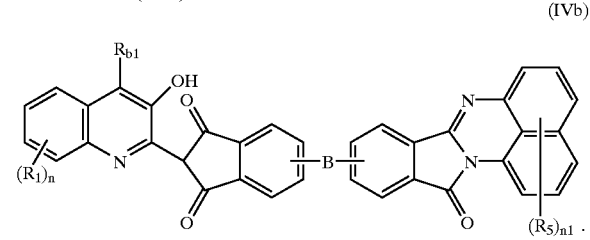

(IVb)

29. Process for preparing the compounds of the formula (I) comprising condensing tetracarboxylic acids of the formula (V) or anhydrides formed from them,

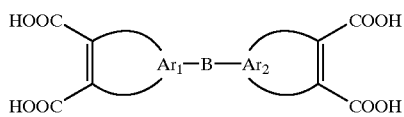

(V)

with one or more compounds of the formulae (VI) and/or (VII)

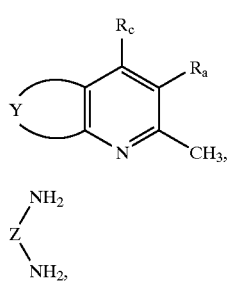

where
$R_c$ is H, COOH or halogen,
the sum total of the compounds of the formulae (VI) and (VII) being equal to two mole equivalents, based on tetracarboxylic acid (V).

30. A process for mass coloration of plastics comprising incorporating the compound of claim 1 into the plastics or starting components of the plastics.

31. The process according to claim 30, wherein the plastic is a thermoplastic.

32. The process according to claim 30, wherein the plastic is a vinyl polymer.

33. The process according to claim 32 wherein the vinyl polymer is polystyrene, a polyester or acrylonitrile-butadiene-styrene, styrene-acrylonitrile, polymethyl methacrylate or polycarbonate.

34. Plastics containing a compound according to claim 1.

* * * * *